United States Patent [19]

Child et al.

[11] Patent Number: 4,956,518

[45] Date of Patent: Sep. 11, 1990

[54] HETEROGENEOUS ISOPARAFFIN/OLEFIN ALKYLATION

[75] Inventors: Jonathan E. Child, Sewell; Tai-Sheng Chou, Pennington, both of N.J.; Albin Huss, Jr., Chadds Ford; Clinton R. Kennedy, West Chester, both of Pa.; Francis P. Ragonese, Cherry Hill; Samuel A. Tabak, Wenonah, both of N.J.

[73] Assignee: Mobil Oil Corp., New York, N.Y.

[21] Appl. No.: 377,993

[22] Filed: Jul. 11, 1989

Related U.S. Application Data

[63] Continuation-in-part of Ser. No. 219,129, Jul. 15, 1988, abandoned.

[51] Int. Cl.$^5$ ............................................. C07C 2/58
[52] U.S. Cl. ..................................... 585/726; 585/728
[58] Field of Search ................................. 585/726, 728

[56] References Cited

U.S. PATENT DOCUMENTS

| | | | |
|---|---|---|---|
| 2,284,554 | 5/1942 | Beyerstedt | 585/726 |
| 2,345,095 | 3/1944 | Bruner et al. | 585/726 |
| 2,804,491 | 7/1957 | May et al. | |
| 2,939,890 | 6/1960 | Hervert et al. | |
| 3,131,230 | 4/1964 | Hervert et al. | |
| 3,251,902 | 5/1966 | Garwood et al. | |
| 3,855,342 | 12/1974 | Huang et al. | |
| 3,862,258 | 1/1975 | Huang et al. | |
| 3,893,942 | 7/1975 | Yang | |
| 3,997,621 | 12/1976 | Brennan | |
| 4,308,414 | 12/1981 | Madgavkar et al. | |
| 4,365,105 | 12/1982 | Morganson et al. | |
| 4,384,161 | 5/1983 | Huang | |
| 4,394,296 | 7/1983 | Madgavkar et al. | |

FOREIGN PATENT DOCUMENTS

| | | | |
|---|---|---|---|
| 1118181 | 11/1961 | Fed. Rep. of Germany | 585/726 |
| 546406 | 7/1942 | United Kingdom | 585/726 |

OTHER PUBLICATIONS

Fixed-Bed Catalytic Process to Produce Synthetic Lubricants from Decene-1, (Gulf Research and Development Co.), 1983 American Chemical Society.

Primary Examiner—Curtis R. Davis
Attorney, Agent, or Firm—Alexander J. McKillop; Charles J. Speciale; Robert B. Furr, Jr.

[57] ABSTRACT

An improved continuous process for alkylation of isoparaffins with olefins to yield a product which includes a large proportion of highly branced paraffins for making gasoline having improved octane is taught. The improved process comprises contacting isoparaffins and olefins with a composite catalyst comprising a Lewis acid and a non-zeolitic inorganic oxide in the presence of a controlled amount of water. The process results in reduced catalyst aging and obviates environmental problems associated with prior art processes.

19 Claims, 1 Drawing Sheet

EFFECT OF H2O ADDITION ON BF3/SiO2 CATALYST

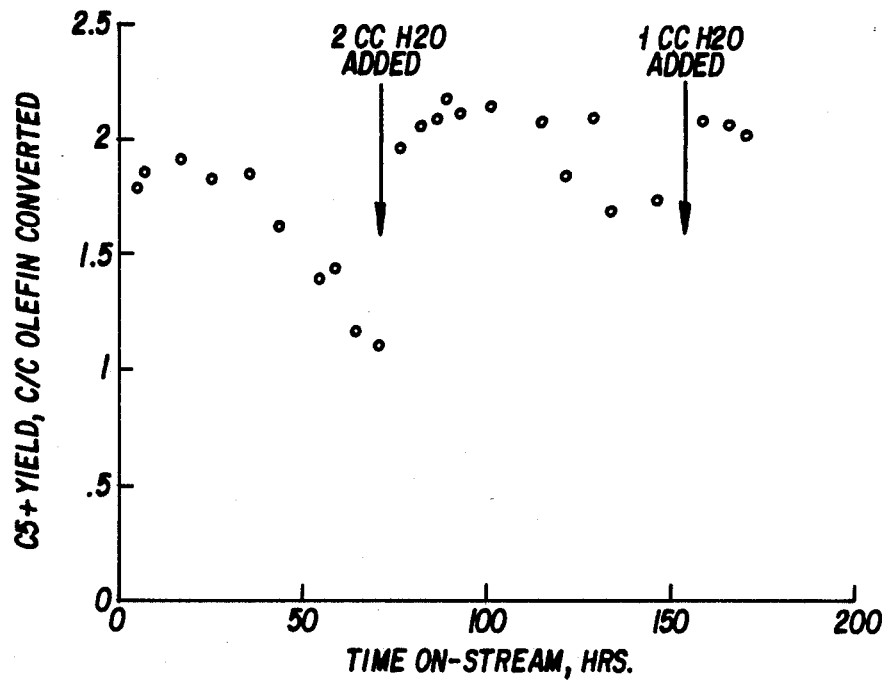
FIG. 1 EFFECT OF H2O ADDITION ON BF3/SiO2 CATALYST
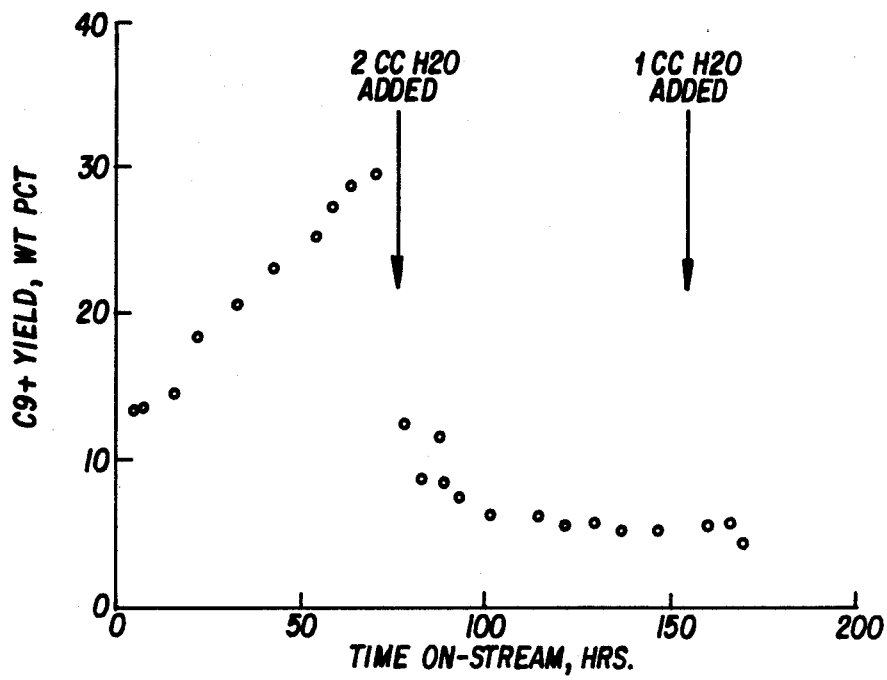
FIG. 2 EFFECT OF H2O ADDITION ON BF3/SiO2 CATALYST

HETEROGENEOUS ISOPARAFFIN/OLEFIN ALKYLATION

RELATED APPLICATIONS

This application contains related subject matter with applications Ser. No. 219,130, now abandoned, entitled Heterogeneous Isoparaffin/Olefin Alkylation Process; and application Ser. No. 219,527, now U.S. Pat. No. 4,918,255, entitled Heterogeneous Isoparaffin/Olefin Alkylation Process with Isomerization, all filed of even date, July 15, 1988.

This application is a continuation-in-part of application Ser. No. 219,129, filed July 15, 1988, and now abandoned. All of the applications are hereby incorporated by reference.

FIELD OF THE INVENTION

The present invention relates to the art of improving octane rating of gasoline by continuously alkylating an isoparaffin with an olefin to provide an alkylate product useful as a high octane blending component in gasoline.

BACKGROUND OF THE INVENTION

This invention results from a need to improve octane ratings for gasoline. Isoparaffin-olefin alkylation is a means to produce highly branced paraffins which effect the octane improvement, which is the objective of this invention.

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This is a very valuable blending component in the manufacture of gasoline because of its high octane rating.

Traditionally, the process in the industry includes the use of hydrofluoric acid or sulfuric acid as catalysts under controlled temperature conditions. Low temperatures are utilized in the sulfuric acid process to minimize the side reaction of olefin polymerization, and the acid strength is generally maintained at 88 to 94% by the continuous addition of fresh acid and the continuous withdrawal of spent acid. The hydrofluoric acid process is less temperature-sensitive and the acid is easily recovered and purified.

The typical types of alkylation currently used to produce high octane gasoline blending components, that is, the hydrofluoric acid and sulfuric acid alkylation processes, have inherent drawbacks including environmental concerns, acid consumption and sludge disposal. With the increasing demands for octane and the increasing environmental concerns, it has been desirable to develop an alkylation process based on a solid catalyst system. The catalyst of the present invention offers a refiner a more environmentally acceptable and more selective alkylation process than the currently used hydrofluoric and sulfuric acid alkylation processes.

Although alkylation processes using liquid, acidic catalysts are commercially successful, inherent disadvantages arise, in addition to those mentioned above, in the use of such catalysts including handling and disposal of corrosive material.

Consequently, substantial efforts have been made to develop a viable isoparaffin-olefin alkylation process using a solid catalyst which is commercially acceptable.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as waterforming compound.

U.S. Pat. No. 4,384,161 describes a process of alkylating isoparaffins with olefins to provide alkylate using as a catalyst a large pore zeolite capable of absorbing 2,2,4-trimethylpentane and a Lewis acid such as boron trifluoride, antimony pentafluoride or aluminum trichloride. The use of a large pore zeolite in combination with the Lewis acid is reported to greatly increase the activity and selectivity of the zeolite thereby effecting alkylation with high olefin space velocity and low isoparaffin-/olefin ratio. According to the patent, problems arise in the use of solid catalysts in that they appear to age rapidly and cannot perform effectively at high olefin space velocity and the patent teaches the above solution to rectify the problem utilizing a zeolite type catalyst.

The article entitled *Fixed Bed Catalytic Process To Produce Synthetic Lubricants From Decene-1*, Ind. Eng. Chem. Prod. Res. Dev., Vol. 22, No. 4 (1983), teaches oligomerizing olefins to produce fluids with lubricating properties using a silica-$BF_3$- water catalyst. The authors further teach that with this system much of the $BF_3$ can be recycled to minimize $BF_3$ consumption and disposal problems. The reference teaches that water is a necessary component of the system and that in its absence a $BF_3$-silica catalyst rapidly deactivates. The reference further teaches that for less reactive olefins, such as Decene-1, a useful degree of oligomerization is achieved only by adding a measurable quantity of an activator such as water or a primary alcohol to $BF_3$. The authors further point out that other $BF_3$ activators, such as esters, ketones, acids and anhydrides, have also been claimed to form good olefin oligomerization catalysts. The article states that the process disclosed there is to both minimize $BF_3$ consumption and disposal problems to produce a product having excellent lubricating properties through use of a catalyst requiring an activator like water.

In U.S. Pat. No. 4,308,414, an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 4,429,177 further relates to a method for making lubricating oil utilizing a catalyst comprising boron trifluoride, a minute amount of elemental oxygen and a particulate absorbent material such as silica. The reference points out that the two component catalysts comprising a solid absorbent and boron trifluoride gradually lose activity after a period of continued use, which aging cannot be conveniently corrected by increasing the boron trifluoride pressure. As a solution, the reference teaches that this aging can be essentially prevented if a minute amount of elemental oxygen is fed to the reactor.

U.S. Pat. No. 3,997,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105, also relates to oligomerizing an olefin in the presence of three-component catalyst comprising a particulate solid absorbent, boron trifluoride and elemental oxygen to make lubricating oils.

U.S. Pat. No. 4,394,296 relates to a three-component catalyst used in making lubricating oils which comprises a particular silica absorbent with boron trifluoride and water absorbed on the silica.

U.S. Pat. No. 2,939,890 discloses a process for alkylating an aromatic hydrocarbon with an olefin-acting compound at alkylation conditions in the presence of an alkylation catalyst comprising boron trifluoride modified alumina. Subsequently, U.S. Pat. No. 3,131,230 discloses the importance of the presence of small amounts of water for maintaining catalyst activity. Both of these patents are limited to aromatic alkylation processes.

U.S. Pat. No. 2,804,491 relates to an isoparaffin/olefin alkylation to make gasoline at temperatures between $-20°$ and $150°$ F. utilizing a two component catalyst comprising essentially excess $BF_3$ with a "silica stabilized gel amumina". No activators are taught.

In the past, severe activity and stability problems have been noted for zeolite based systems. U.S. Pat. Nos. 3,251,902 and 3,893,942, as well as French Patent No. 1,598,716 and the article to Kirsh and Potts, Div. of Pet. Chem. A.C.S., 15, A109 (1970) exemplify these problems. Improved stability was noted when a Lewis acid such as $BF_3$ was used in combination with macroreticular acid cation exchange resins as pointed out in U.S. Pat. No. 3,855,342. More recently, the use of $BF_3$ in combination with large pore zeolites such as ZSM-4 and Beta has been reported to effectively catalyze isoparaffin/olefin alkylation reactions. See U.S. Pat. No. 4,384,161.

However, only applicants have achieved advantages compared to these previous teachings by use of a catalyst comprising Lewis acids, such as $BF_3$, in combination with nonzeolitic solid inorganic oxides, such as $SiO_2$ or $Al_2O_3$, in the presence of controlled amounts of water to produce higher octane gasoline and to reduce catalyst aging compared to these earlier processes.

Thus, this invention overcomes the problems posed by the prior art in that catalyst aging is significantly reduced. The present process effects improved octane ratings for gasolines by utilizing a heterogeneous catalyst in the presence of water.

The preceding references are hereby incorporated by reference.

SUMMARY OF THE INVENTION

This invention relates to an alkylation process for producing high octane gasoline comprising effecting reaction of an isoparaffin containing from 4 to 20 carbon atoms with an olefin containing from 2 to 12 carbon atoms at from about $-40°$ C. to about $500°$ C. and at a pressure in the range of subatmospheric to about 5000 psig using a hydrocarbon feed wherein the molar ratio of the isoparaffin to the olefin in the combined hydrocarbon feed is from about 0.5:1 to about 200:1 in contact with a composite catalyst comprising a Lewis acid with a nonzeolitic solid inorganic oxide in the presence of water.

This invention also relates to an alkylation process for producing high octane gasoline comprising effecting reaction of an isoparaffin containing from 4 to 20 carbon atoms with an olefin containing from 2 to 12 carbon atoms at from about $-40°$ C. to about $250°$ C. and at a pressure from about subatmospheric to about 500 psig using a reaction mixture containing about 0.1 ppmw to about 500 ppmw $H_2O$ based on total hydrocarbon feed and having a molar ratio of the isoparaffin to the olefin from about 5:1 to about 25:1 in contact with a composite catalyst comprising $BF_3$ with a non-zeolitic solid inorganic oxide.

BRIEF DESCRIPTION OF THE DRAWINGS

FIG. 1 shows the effect of $H_2O$ addition on catalyst aging as measured by $C_5+$ yield.

FIG. 2 shows the effect of $H_2O$ addition on catalyst aging as measured by $C_9+$ yield.

DESCRIPTION OF THE INVENTION

The alkylation of isobutane with light olefins plays an important role in the manufacture of high octane gasoline blending stocks with alkylate typically comprising 10 to 15% of the gasoline pool. Alkylate is a particularly valuable portion of the gasoline pool as it has both high research and motor octane, contains no olefins or aromatics and little or no sulfur, demonstrates excellent stability and is clean burning.

Applicants have developed a process for producing high octane gasoline. It includes a novel isoparaffin/olefin alkylation catalyst. The catalyst system includes a Lewis acid, such as $BF_3$, in combination with a non-zeolitic solid inorganic oxide, such as $SiO_2$, to promote paraffin/olefin alkylation, all in the presence of a controlled amount of water. The Lewis acid is to be maintained at a level in excess of that required to saturate the non-zeolitic solid inorganic oxide. The resulting alkylate is of a high quality based on both research and motor octane and is particularly suited for blending into a gasoline pool.

Consider the catalyst comprising the Lewis acid and inorganic oxide. A Lewis acid is generally considered to be a molecule which is capable of combining with another molecule or ion by forming a covalent chemical bond with two electrons from the second molecule or ion, that is to say, the Lewis acid is an electron acceptor. Examples of Lewis acids include boron trifluoride ($BF_3$), boron trichloride ($BCl_3$), antimony pentafluoride ($SbF_5$), and aluminum choloride ($AlCl_3$). The present invention contemplates the use of all Lewis acids, such as those set forth in *Friedel-Crafts and Related Reactions*, Interscience Publishers, chapters III and IV (1953), which is incorporated by reference.

The inorganic oxide of this catalyst may be selected from among the diverse inorganic oxides including alumina, silica, boria, oxides of phosphorus, titanium dioxide, zirconium dioxide, chromia, zinc oxide, magnesia, calcium oxide, silica-alumina, silica-magnesia, silica-alumina-magnesia, silica-alumina-zirconia, chromia-alumina, alumina-boria, silica-zirconia, etc. and the various naturally occuring inorganic oxides of various states of purity such as bauxite, clay, diatomaeous earth, etc. The preferred inorganic oxides are amorphous silicon dioxide and aluminum oxide.

The operating temperature of the alkylation process can extend over a fairly broad range, for example, from about $-40°$ C. to about $500°$ C. and is preferably with the range of from about $-40°$ C. to about $250°$ C. The practical upper operating temperature will often be dictated by the need to avoid an undue occurrence of undesirable side reactions.

The pressures used in the present process can extend over a considerably wide range, for example, from sub-atmospheric to about 5000 psig, preferably to about 500 psig.

The amount of catalyst used in the present process can be varied over relatively wide limits. In general, the amount of catalyst, as measured by the weight hourly space velocity of the olefin, can range from about 0.01 to about 100. It will be realized by those skilled in the art that the amount of catalyst selected for a particular reaction will be determined by several variables including the reactants involved as well as the nature of the catalyst and the operating conditions used.

The particular operating conditions used in the present process will depend on the specific alkylation reaction being effected. Such conditions as temperature, pressure, space velocity and molar ratio of the reactants will have important effects on the overall process. Also, the operating conditions for the alkylation reaction according to this process may be varied so that the same may be conducted in gaseous phase, liquid phase or mixed liquid-vapor phase, depending upon product distribution, degree of alkylation, as well as the pressures and temperatures at which the alkylation is effected.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant used generally contains from 2 to about 12 carbon atoms. Representative examples are ethylene, propylene, butene-1, butene-2, isobutylene, and pentenes, etc. Particularly preferred are $C_3$ and $C_4$ olefins and mixtures thereof.

In general, the relative molar ratio between the isoparaffin reactant and the olefin alkylating agent can be from about 0.5:1 to about 200:1 and is preferably in the range of from about 5:1 to about 25:1. However, in one embodiment the molar ratio is from about 0.5:1 to about 5:1.

A critical requirement of the improved alkylation process herein is that water be added continuously to the alkylation reactor, that is, at a rate on average of from about 0.1 ppmw to about 1 wt. % based upon total hydrocarbon feed rate, preferably at a rate from about 0.1 to about 500 ppmw. The water can be supplied as such or be a feed material which provides water under the alkylation condition selected. Suitable water-forming materials which can be introduced into the reactor without interfering with the desired alkylation include monohydric and dihydric alcohols which yield water upon undergoing dehydration. Of this group, particular preference is accorded the aliphatic alcohols, especially those containing 1 to 6 carbon atoms, for example, methanol, ethanol, isopropanol, t-butyl alcohol and isopentyl alcohol.

EXPERIMENTATION

The following examples will serve to illustrate the process of the invention without limiting it. The data presented below in Examples 1 and 2 demonstrate the improved octane and reduced catalyst aging which result from the addition of water to the composite catalyst system comprising a Lewis acid in combination with a non-zeolitic solid inorganic oxide.

EXAMPLE 1

This examples illustrates the effect of continuous $H_2O$ addition on the resulting alkylate quality. The specific alkylation operating conditions used in the examples are set forth in Table 1.

TABLE 1

| $BF_3$ PROMOTED ALKYLATION OPERATING CONDITIONS | |
|---|---|
| Temperature, °C. | 20 |
| Pressure, psig | 150 |
| Stirring Rate, rpm | 1900 |
| $BF_3$ Feed Rate, wt % of HC Feed | 3.0 |
| HC Feed, i-$C_4$/olefin ratio | 10/1 |
| Olefin WHSV, $hr^{-1}$ | 1.2 |
| MIXED $C_3/C_4$ OLEFIN DISTRIBUTION, WT % | |
| Propylene | 42.5 |
| 1-Butene | 13.7 |
| Cis + Trans-2-Butene | 28.2 |
| Isobutylene | 15.6 |

The non-zeolitic solid inorganic oxide used in this example is a commercially available amorphous $SiO_2$ (0.5 weight % $Al_2O_3$). The as-received material is calcined at 1000° F. and sized to 100/200 mesh before use in the alkylation reactor.

In a standard start-up procedure, 10 grams of catalyst is placed in the 300 ml autoclave reactor, and about 300 ml of isobutane is charged to fill the reactor. The resulting mixture is cooled to the desired temperature with constant stirring at 1900 rpm and $BF_3$ gas is introduced continuously into the reactor. After $BF_3$ breakthrough is observed, the $BF_3$ flow rate is then reduced to a level equivalent to 3 wt % of total hydrocarbon feed rate. At this point, the isobutane/olefin mixture is continuously fed into the reactor to initiate the catalytic alkylation. The feed is a simulated commercial feed (approximately 10/1 i—$C_4$/mixed olefins) approximating the $C_3^=/C_4^=$ fraction produced from an FCC. The operating conditions as set forth in Table 1 are 150 psig, 20° C., 1900 RPM, 1.2 WHSV based on olefin and 3.0 wt % $BF_3$ based on total hydrocarbon feed rate. The product is continuously withdrawn from the reactor and is weathered to atmospheric pressure via a back pressure regulator and then sent to a receiver which is kept at 0° C. Periodically, the product is drained from the receiver and weathered at room temperature prior to analysis.

An on-line gas chromatograph coupled with an automatic sampling device is used to monitor the course of the alkylation reaction. All reported octane numbers are measured. The isobutane (C.P. grade), isobutane/mixed $C_3+C_4$ olefins and $BF_3$ (C.P. grade) are used without further purification.

The resulting yield and octane data for the $BF_3/SiO_2$ catalyst system, summarized in Table 2, shows a comparison between alkylation with and without added water. These two runs are designated in Table 2 as Examples 1B and 1A, respectively. In case of water addition (Example 1B), water is added intermittently throughout the run at an average rate of about 100 ppmw based upon total hydrocarbon feed rate.

TABLE 2

| THE EFFECT OF WATER ADDITION ON $BF_3$-PROMOTED ALKYLATION | | |
|---|---|---|
| Example | 1A $BF_3/SiO_2$ | 1B $BF_3/SiO_2/H_2O$ |
| Catalyst System Yield, g $C_5+$/g Olefin Converted | 2.1 | 2.1 |

TABLE 2-continued

THE EFFECT OF WATER ADDITION ON
BF$_3$-PROMOTED ALKYLATION

| Example | 1A<br>BF$_3$/SiO$_2$ | 1B<br>BF$_3$/SiO$_2$/H$_2$O |
|---|---|---|
| Yields in C$_5$+, Wt % | | |
| C$_5$ | 3.4 | 2.7 |
| C$_6$ | 3.3 | 2.3 |
| C$_7$ | 29.1 | 27.1 |
| C$_8$ | 54.7 | 61.4 |
| C$_9$+ | 9.6 | 6.4 |
| RON + O | 91 | 93 |
| MON + O | 89 | 90 |

The results show that aklylation is essentially complete in both cases based upon the high C$_5$+ yield per g of olefin converted. However, low level H$_2$O addition substantially improves alkylate quality over BF$_3$/silica catalyst alone as seen by the increased research and motor octanes and reduced C$_9$+ yield.

EXAMPLE 2

Example 1 is repeated except that the reaction temperature is 0° C. and the catalyst is different: BF$_3$/ SiO$_2$ (0.2 wt. percent Al$_2$O$_3$). The purpose of this experiment is to show the effect of intermittent H$_2$O addition on catalyst aging. The experiment is conducted without H$_2$O addition until time onstream is about 75 hours. At that point, 2 cc H$_2$O are added. Thereafter, 1 cc of H$_2$O is added at about 155 hours. During the reaction the C$_5$+ and C$_9$+ yields are measured and the results are shown in FIGS. 1 and 2, respectively. In FIG. 1, the C$_5$+ yield progressively degrades to about 1 g C$_5$+/g olefin converted until 2.0 cc of water is added at about 75 hours into the reaction. At this point, the C$_5$+ yield increases dramatically to 2.1 g C$_5$+/g olefin converted, indicating complete alkylation is restored. At about 155 hours into the reaction, an additional 1 cc of H$_2$O is added to further extend the cycle length. FIG. 2 shows that the addition of H$_2$O inhibits C$_9$+ formation, presumably by minimizing undesireable side reactions, e.g. polymerization. Thus, addition of H$_2$O in an alkylation reaction using a BF$_3$/ SiO$_2$ catalyst system significantly reduces catalyst aging.

Commerical processes for alkylation of isobutane with propene and butenes require high isobutane to olefin feed ratios (I/O) to maintain high octane products. Low isobutane to olefin ratios, that is, between about 0.5:1 to about 5:1, produce high levels of C$_9$+ fraction with octanes around 70 while high I/O ratios, that is, from about 5:1 to 25:1 and above, suppress the formation of the undesireable C$_9$+ material. Quite unexpectedly, applicants have found that the C$_9$+ fraction produced from isobutane/olefin alkylation using BF$_3$-promoted silica catalysts has octanes above about 85. This permits operation at heretofore unacceptably low isobutane to olefin ratios. Because the C$_9$+ fraction is formed from less than one mole of isobutane per mole of olefin, this system also permits complete olefin conversion to gasoline when stoichiometric amounts of isobutane are not available. This offers the refiner a process with significantly improved flexibility when isobutane availability is limited.

The discovery of high octane C$_9$+ products from alkylation of isobutane with olefins using a BF$_3$-promoted silica catalyst is both new and unexpected. The C$_9$+ fraction produced from alkylation with hydrofluoric acid or sulfuric acid, the two existing commercial processes, are low octane and therefore detrimental to the alkylate quality.

In the process of this embodiment of the present invention, applicants propose using a BF$_3$-promoted solid catalyst system with the I/O ratios well below that of current commercial processes. The resulting product has a substantial fraction of C$_9$+ components and yet quite unexpectedly has a high octane.

EXAMPLES 3 & 4

Example 1 is repeated with the exceptions noted below. Table 3 shows the resulting octane/boiling point distributions for alkylate samples from continuous pilot unit runs using BF$_3$ promoted silica in both a slurry unit (Example 3) and a fixed bed unit (Example 4). Both examples were carried out at 0° C. and 150 psig using a 10/1 isobutane/2-butene feed. The slurry unit evaluation of Example 3 also included intermittent H$_2$O addition at an equivalent of approximately 100 ppmw based on total hydrocarbon feed rate. The results show that as the C$_9$+ fraction of the alkylate increases from 11.5 to 67.6 wt % in going from Example 3 to Example 4, the research octane number (RON) of the full range gasoline is uneffected while the motor octane number (MON) decreases only slightly. In both cases, the full range gasoline octanes are above 90. Furthermore, the RON of the C$_9$+ fraction is nearly 85 in the case of Example 3 and over 95 for Example 4. The relatively high octanes of the C$_9$+ fractions indicate that operation at heretofore unacceptably low I/O ratios is possible with the catalyst system of the present invention. Low I/O ratio operation favors high C$_9$+ yields with low isobutane consumption. By comparison, Table 3 also shows the octane/boiling point distribution for several commercial alkylates. The octane of the C$_9$+ fractions are all quite low for the commercial alkylates. These low octanes make operation of a commercial HF unit at low I/O ratios unattractive since these conditions favor production of the low octane C$_9$+ fraction.

TABLE 3

OCTANE/BOILING POINT DISTRIBUTIONS FOR
VARIOUS ALKYLATE SAMPLES

| | Boiling Point Distribution, wt % | Octanes | |
|---|---|---|---|
| | | RON | MON |
| Example 3 Alkylate | | | |
| Full Range Alkylate | 100.0 | 97.0 | 94.0 |
| IBP – 265° F. | 85.8 | 97.3 | — |
| 265 – 350° F. | 2.7 | 88.8 | — |
| 350° F.+ (C$_9$+) | 11.5 | 84.5 | 88.1 |
| Example 4 Alkylate | | | |
| Full Range Alkylate | 100.0 | 97.2 | 91.1 |
| IBP – 265° F. | 24.0 | — | — |
| 265 – 350° F. | 8.4 | 87.4 | — |
| 350° F.+ (C$_9$+) | 67.6 | 96.7 | 92.6 |
| Commercial HF Alkylate 1 | | | |
| Full Range Alkylate | 100.0 | 93.7 | 92.0 |
| IBP – 265° F. | 87.4 | 95.0 | — |
| 265 – 350° F. | 7.4 | 78.6 | — |
| 350° F.+ (C$_9$+) | 5.2 | 66.5 | — |
| Commercial HF Alkylate 2 | | | |
| Full Range Alkylate | 100.0 | 90.3 | 89.9 |
| IBP – 265° F. | 85.0 | 93.2 | 92.0 |
| 265° F.+ (C$_9$+) | 15.0 | 68.0 | 68.0 |

In a commercial plant, the flexibility to operate at reduced isobutane consumption can be obtained automatically. As the isobutane to olefin ratio drops below the stoichiometric amount, the isobutane consumption will initially exceed the isobutane makeup. This will decrease the isobutane available for recycle, resulting in a reduced isobutane to olefin ratio. The low isobutane to olefin ratio causes $C_9+$ oligomer yield to increase, thereby decreasing the isobutane consumption. The whole system will reach a new equilibrium where the isobutane consumption equals the isobutane makeup.

Although the invention has been described in conjunction with specific embodiments, it is evidence that many alternatives and variations will be apparent to those skilled in the art in light of the foregoing description. Accordingly, the invention is intended to embrace all of the alternatives and variations that fall within the spirit and scope of the appended claims.

We claim:

1. A continuous alkylation process for producing high octane gasoline comprising effecting reaction of an isoparaffin containing from 4 to 20 carbon atoms with an olefin containing from 2 to 12 carbon atoms at from about $-40°$ to about $500°$ C. and at a pressure in the range of subatmospheric to about 5000 psig using a hydrocarbon feed wherein a molar ratio of the isoparaffin to the olefin in the hydrocarbon feed is from about 0.5:1 to about 200:1 in contact with a composite catalyst comprising a Lewis acid with a non-zeolitic solid inorganic oxide in the presence of water wherein a molar ratio of the water to said Lewis acid is less than about 1:1.

2. The process of claim 1, wherein the isoparaffin contains from 4 to 6 carbon atoms and the olefin contains from 2 to 6 carbon atoms.

3. The process of claim 1, wherein the Lewis acid is $BF_3$, $BCl_3$, $SbF_5$ and/or $AlCl_3$.

4. The process of claim 1, wherein the Lewis acid is $BF_3$.

5. The process of claim 1, wherein the inorganic de is $SiO_2$ or $Al_2O_3$.

6. The process of claim 1, wherein the catalyst is $BF_3/SiO_2$.

7. The process of claim 1, wherein the reaction is conducted under sufficient pressure to maintain at least one of the reactants in the liquid phase.

8. The process of claim 1, wherein the molar ratio of the isoparaffin to the olefin is from 5:1 to about to 25:1.

9. The process of claim 1, wherein the isoparaffin is isobutane and the olefin is propylene and/or butenes.

10. The process of claim 1, wherein the water and/or water-producing material is cofed with the reactants.

11. The process of claim 10, wherein the amount of water ranges from about 0.1 ppmw to about 1 weight percent based upon the total hydrocarbon feed rate.

12. The process of claim 10, wherein the amount of water ranges from about 0.1 ppmw to about 500 ppmw based upon the total hydrocarbon feed rate.

13. The process of claim 1, wherein water is added intermittently to the reaction.

14. The process of claim 1, wherein the reaction temperature is from about $-40°$ C. to about $250°$ C.

15. The process of claim 1, wherein the weight hourly space velocity of the olefin is from about 0.01 to about 100.

16. The process of claim 1, wherein the Lewis acid is present in an amount in excess of that required to saturate the non-zeolitic solid inorganic oxide.

17. The process of claim 1, wherein the molar ratio of the isoparaffin to the olefin is from about 0.5:1 to about 5:1.

18. A continuous alkylation process for producing high octane gasoline comprising effecting reaction of an isoparaffin containing from 4 to 20 carbon atoms with an olefin containing from 2 to 12 carbon atoms at from about $-40°$ C. to about $250°$ C. and at a pressure from about subatmospheric to about 500 psig using a reaction mixture containing about 0.1 ppmw to about 500 ppmw $H_2O$ based on total hydrocarbon feed and having a molar ratio of the isoparaffin to the olefin from about 5:1 to about 25:1 in contact with a composite catalyst comprising $BF_3$ with a non-zeolitic solid inorganic oxide.

19. The process of claim 18, wherein the Lewis acid is present in an amount in excess of that required to saturate the non-zeolitic solid inorganic oxide.

* * * * *